United States Patent
Kaneko

[11] Patent Number: 5,854,668
[45] Date of Patent: Dec. 29, 1998

[54] OPHTHALMOSCOPIC CAMERA ILLUMINATION APPARATUS

[75] Inventor: Masanobu Kaneko, Yokohama, Japan

[73] Assignee: Nikon Corporation, Tokyo, Japan

[21] Appl. No.: 896,361

[22] Filed: Jul. 18, 1997

[30] Foreign Application Priority Data

Feb. 6, 1997 [JP] Japan .................................. 9-038384

[51] Int. Cl.⁶ ...................................................... A61B 3/14
[52] U.S. Cl. ........................................... 351/206; 351/221
[58] Field of Search .................................... 351/206, 221, 351/205, 200, 246, 207; 354/62

[56] References Cited

U.S. PATENT DOCUMENTS 4,502,766 3/1985 Ito ............................................ 351/206

FOREIGN PATENT DOCUMENTS

U 58-185819 12/1983 Japan .

*Primary Examiner*—Hung X. Dang
*Attorney, Agent, or Firm*—Michael N. Meller

[57] ABSTRACT

A compact ophthalmoscopic camera illumination apparatus with which a bright eyeground image can be obtained even for high magnification photography. The camera includes an annular flux forming means that has an entering end (22A) positioned in a vicinity of a light source image, an annular emitting end (22D), a cone-shaped outer reflective surface (22B), and a cone-shaped inner reflective surface (22C); wherein illumination light entering the entering end is reflected on the outer reflective surface and the inner reflective surface, guided to the emitting end, and exits as annular flux from the emitting end. The annular flux passes through the objective lens (1) to form an annular illumination area in the vicinity of the pupil (20) of the patient's eye.

11 Claims, 4 Drawing Sheets

OPHTHALMOSCOPIC CAMERA ILLUMINATION APPARATUS

BACKGROUND OF THE INVENTION

1. Field of the Invention

The present invention relates to an ophthalmoscopic illumination apparatus; more specifically, it relates to an illumination apparatus which illuminates a fundus of a patient's eye for an ophthalmoscopic camera that photographs the fundus of the patient's eye.

2. Background Prior Art

In a conventional ophthalmoscopic device such as an ophthalmoscopic camera in particular, an annular illumination has been used to avoid a reflection from cornea of a patient's eye.

In the annular illumination apparatus, an annular slit is normally arranged in conjugation with the patient's eye; of the light beams emitted from a light source, only the light beams passing through an annular aperture of the annular slit are picked up near the pupil of the patient's eye to illuminate the fundus. "Fundus" is defined by the Random House Dictionary of the English language 1967 as "the base of an organ or the part opposite to or remote from an aperture". Here, the annular slit is almost in conjugation with the light source via a condenser lens. The shape of the light source such as a lamp light source for observation and strobe light source for photographing is normally not annular. Consequently, the light beams in the center of the illumination light, where the light is the brightest, are shielded by a shutter unit of the annular slit, resulting in inefficient use of the illumination light.

Also, the reflective coefficient of the fundus of the patient's eye is extremely small; with higher magnification, the image of the fundus is dimmed, thus making highly magnified photographing impossible. In addition, introducing a larger output from a light source which will obtain a brighter eyeground image requires an unfavorably larger power supply unit or generates unfavorable heat from the light source.

An ophthalmoscopic illumination apparatus was proposed in Japanese Laid-Open Patent Application No. 56-163629 assigned to the assignee of the present invention to solve the above mentioned problems. In the conventional ophthalmoscopy illumination apparatus proposed in this earlier specification, an optical fiber having an entering surface whose shape is similar to that of the light source and an annular emitting surface is arranged between a condenser lens and a relay lens. This apparatus forms a light source image at the entering surface of the optical fiber via the condenser lens, and then supplies annular light beams from the emitting surface of the optical fiber.

In the above mentioned conventional ophthalmoscopic illumination apparatus, the optical fibers are composed of a bundle of fine fibers. For this reason, the density loss is caused due to the gap between the fibers or multiple reflections within the fibers, resulting in obtaining illumination light of insufficient brightness.

Further, an optical fiber is not structurally flexible to be bent to a large degree. As a result, in the conventional ophthalmoscopic illumination apparatus, having the optical fibers in the optical path of the illumination system inevitably requires a large illumination system.

SUMMARY OF THE INVENTION

The present invention intends to resolve the aforementioned problems.

Another purpose of the present invention is to provide a compact ophthalmoscopic illumination apparatus with which a bright eyeground image can be obtained without a large power source even for high magnification photography; a reasonably bright eyeground image can be obtained with smaller energy consumption for low magnification photography.

In order to attain the aforementioned purposes, the present invention provides an ophthalmoscopic illumination apparatus, which illuminates the fundus of an patient's eye for an ophthalmoscopic camera to photograph the fundus through an objective lens, the apparatus comprises:

a light source for supplying illumination light;

a condensing optical system for gathering the illumination light from the light source to form a light source image; and an annular flux forming means comprising an entering end positioned in the vicinity of a light source image forming position, an annular emitting end, an outer reflective surface formed connected between an outer periphery of the emitting end and the outer periphery of the entering end, and an inner reflective surface formed inside the outer reflective surface so as to be connected to the inner periphery of the emitting end, so that the illumination light entering the entering end is reflected at the outer reflective surface and the inner reflective surface, and guided to the emitting end to exit as annular flux from the emitting end; and wherein the annular flux exiting from the emitting end of the annular flux forming means passes through the objective lens to form an annular illumination area in the vicinity of the pupil of the patient's eye.

According to a preferred mode of the present invention, the angle made by the outer reflective surface with the optical axis is larger than that an angle between the inner reflective surface with the optical axis. Note that the annular flux forming means may be constructed such that a space between the outer reflective surface and the inner reflective surface is made hollow or filled. Also, it is preferable that the annular flux forming means is constructed switchable with another annular flux forming means having a different diameter of the emitting end.

The present invention comprises an annular flux forming means which has, for example, a circular entering end aligned almost in conjugation with a light source image and an annular emitting end aligned almost in conjugation with a pupil of the patient's eye. Note that a cone-shaped outer reflective surface is formed to connect the outer periphery of the annular emitting end with the outer periphery of the circular entering end, and a cone-shaped inner reflective surface is formed inside the outer reflective surface so as to be connected to the inner periphery of the emitting end. Therefore, the illumination light that enters the entering end of the annular flux forming means is repeatedly reflected on the outer reflective surface and the inner reflective surface, and then emitted as annular flux from the emitting end. The annular light flux exiting from the emitting end of the annular flux forming means forms an annular illumination area in the vicinity of the pupil of the patient's eye through the objective lens which is commonly used in the illumination system and in the photographic observation system.

In other words, the present invention takes the light from the light source image into the entering end of the annular flux forming means without a substantial loss in light intensity. The annular flux forming means guides the light beams from the entering end to the emitting end without a substantial loss of light intensity, and emits them as an annular flux. The out-going annular flux forms an annular illumination area in the vicinity of the pupil of the patient's eye, resulting in broadly illuminating the fundus of the patient's eye.

As described, it is another purpose of the present invention to effectively use the light from the light source without a substantial loss, and to illuminate the fundus with a reasonably bright illumination light. For this reason, a bright eyeground image can be obtained without using a large power source even for high magnification photography. A bight eyeground image can be obtained with less power consumption for low magnification photography. In addition, since the annular flux forming means of the present invention can be configured structurally on a small scale, unlike an apparatus of conventional technology which uses optical fibers of limited flexibility (i.e., low bendable angle, the entire apparatus can be compact.

It is necessary that the angle made by the outer reflective surface with the optical axis is larger than that by the inner reflective surface with the optical path so that the light taken in the entering end of the annular flux forming means can be guided entirely to the emitting end, without returning to the entering end.

In particular, the annular flux forming means may be constructed such that the space between the outer reflective surface and the inner reflective surface is made hollow or filled.

Further, it is preferable that the annular flux forming means may be configured such that another annular flux forming means having a different diameter of the emitting end can be used according to the size of the pupil of the patient's eye.

DRAWINGS

FIG. 1 shows a construction of an ophthalmoscopic illumination apparatus of an embodiment of the present invention as well as a observation system and a photographic system of an ophthalmoscopic camera.

FIGS. 2(A), 2(B) and 2(C) are drawings showing constructions of the cone-shaped reflective member 22 in FIG. 1; FIG. 2(A) shows the shape of the entering end; (2B) shows the shape of the emitting end; and (2C) shows a cross-section of the cone-shaped reflective member 22 and the optical path of the light.

FIG. 3 is a drawing showing the relationship between the apical angle of the cone-shaped outer reflective surface 22B and that of the cone-shaped inner reflective surface 22C in the cone-shaped reflective member 22 of FIG. 1; and FIG. 4 is a drawing which shows a configuration of a modified example of the embodiment in FIG. 1.

DETAILED DESCRIPTION

Figure 1:
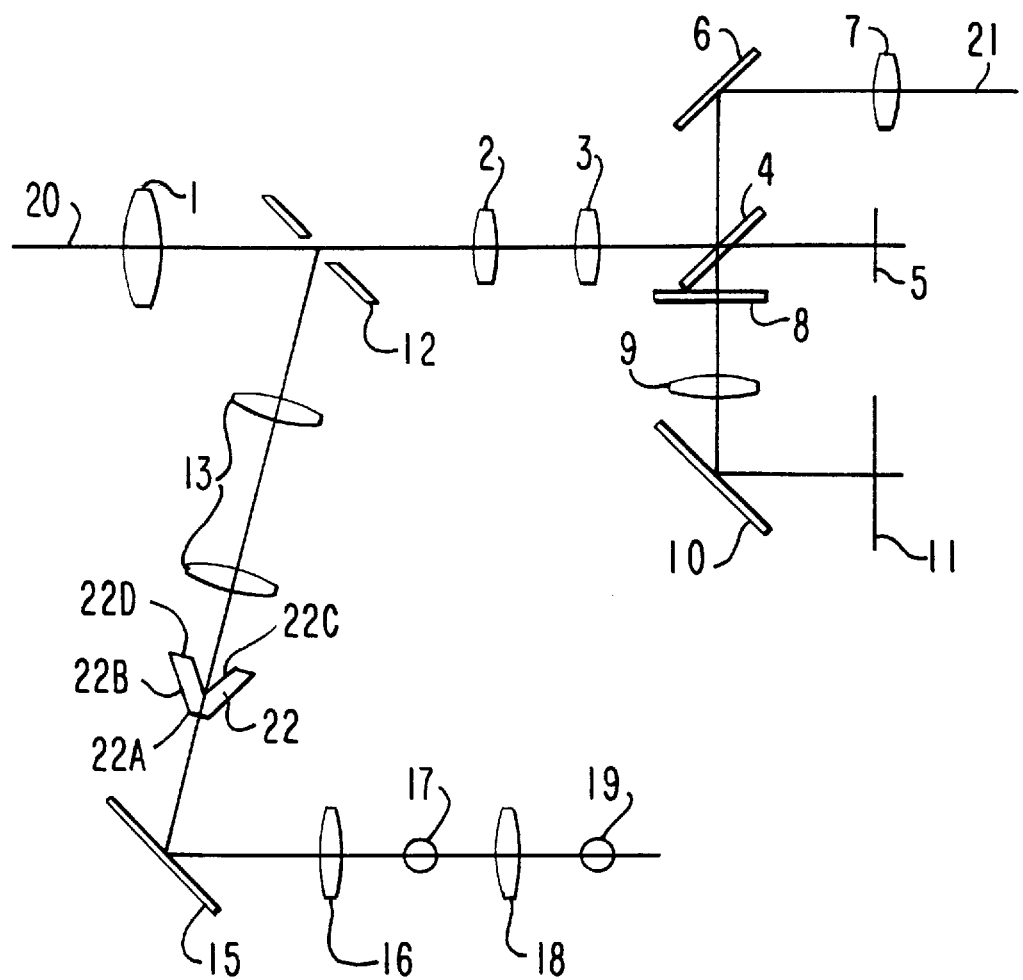

The apparatus of FIG. 1 has a light source for observation 19 such as a lamp light source. Illumination light emitted from the light source for observation 19 is gathered through a condenser lens 18 at a light source for photographing 17 which is almost in conjugation with the light source for observation 19. Note that the light source for photographing 17 is, for example, a strobe light source. The illumination light emitted from the light source for photographing 17 is equivalent to the illumination light emitted from the light source for observation 19, and they are treated as the same illumination light in the illumination system in the description hereinafter.

Figure 2A:
Figure 2B:
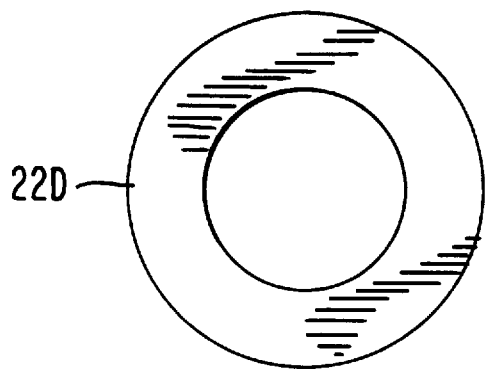
Figure 2C:
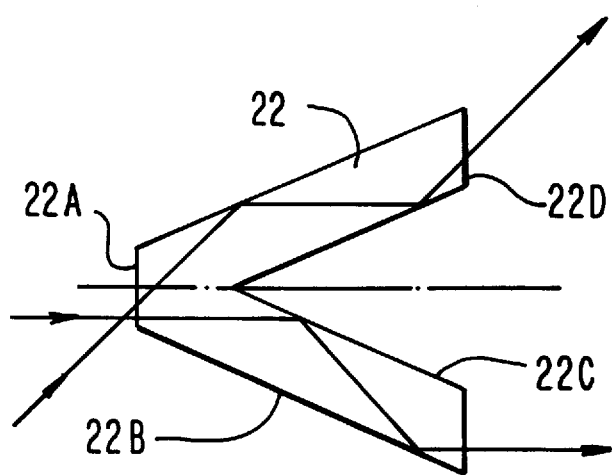

Continuing to refer to FIG. 1, the illumination light emitted from the light source for photographing 17 or the light source for observation 19 passes through a first relay lens 16 and a reflective mirror 15, and then forms a light source image. An entering end 22A of a cone-shaped reflective member 22 is aligned in the vicinity of the position where the light source image is formed. In other words, the light source for observation 19, the light source for photographing 17, and the entering end 22A of the cone-shaped reflective member 22 are in conjugation with one another. In other words, [lit: Therefore], on the entering end 22A of the cone-shaped reflective member 22, a light source image of the light source for observation 19 or the light source for photographing 17 is formed. Note that, as shown in FIG. 2 (*a*), the entering end 22A is circular; it is desirable that the size of the entering end 22A is larger than that of the light source image in order to avoid loss in light intensity. On the other hand, the emitting end 22D of the cone-shaped reflective member 22 is annular as shown in FIG. 2 (*b*).

As shown in FIG. 2 (*c*), a cone-shaped outer reflective surface 22B is formed connecting the outer periphery of the annular emitting end 22D and the outer periphery of the circular entering end 22A. Further, a cone-shaped inner reflective surface 22C is formed inside the outer reflective surface 22B so as to be connected to the inner periphery of the annular emitting end 22D. The space between the outer reflective surface 22B and the inner reflective surface 22C is formed hollow. In other words, the cone-shaped reflective member 22 is a hollow member constructed with a cone-shaped outer cylindrical unit (not illustrated) on which the outer reflective surface 22B is formed and a cone-shaped inner cylindrical unit (not illustrated) on which the inner reflective surface 22C is formed. Note that the reflective surfaces at the inner side of the outer cylindrical unit and the outer side of the inner cylindrical unit are deposited, for example, with evaporated aluminum.

Therefore, as shown in FIG. 2 (*c*), the light beams incident on the entering end 22A are reflected on the inner reflective surface 22C and the outer reflective surface 22B, and exit from the annular emitting end 22D. In this manner, the illumination light entering the entering end 22A is efficiently used without a substantial loss in light density, and exits out as annular flux from the emitting end 22D.

The exiting annular flux from the emitting end 22D of the cone-shaped reflective member 22 passes through a second relay lens 13 and is picked up near a perforated mirror 12. In other words, the emitting end 22D of the cone-shaped reflective member 22 and the perforated mirror 12 are almost in a conjugated relationship. Then, the image of the emitting end 22D of the cone-shaped reflective member 22 is formed on the perforated mirror 12 to be larger than the hole diameter thereof.

The light reflected by the perforated mirror 12 passes through an objective lens 1 to form an annular illumination area at the pupil position of the patient's eye which is almost in conjugation with the perforated mirror 12. That is, the emitting end 22D of the cone-shaped reflective member 22, the perforated mirror 12, and the pupil point 20 of the patient's eye are almost in a conjugated relationship. In this manner, the illumination light entering the patient's eye broadly illuminates the fundus of the patient's eye.

Note that although, in a real ophthalmoscopic camera, a shutter plate is arranged between the cone-shaped reflective member 22 and the second relay lens 13 to avoid a reflection from the crystalline lens of the patient's eye, the plate is not related to the principle of the present invention and is not illustrated.

The light reflected (from the illuminated eyeground of the patient's eye passes through the objective lens which is commonly used for the observing and photographing system) makes an image temporarily, and then passes through the hole in the perforated mirror 12.

In this manner, the illumination light from the light source for observation 19 or the light source for photographing 17 is separated from the reflective light from the fundus of the patient's eye through the effect of the perforated mirror 12. The reflective light passing through the hole in the perforated mirror passes through a photographic relay lens 2 and a variable magnification lens 3 to form a fundus image on a light receiving plane 5 in a first photographing system.

Mirrors 4 and 8 are reflective members for switching the optical paths. When the switching mirror 4 is positioned on the optical path as shown in FIG. 1, the light from the fundus of the patient's eye is guided the observation system by being reflected by the switching mirror 4 and a reflective mirror 6, and then passing through an eyepiece lens 7 to enter the eye of an examiner. In this manner, the examiner can observe the fundus image of the patient's eye by positioning his pupil at an eye point 21 of the eyepiece lens 7.

On the other hand, when the switching mirror 4 is moved away from the optical path and another switching mirror 8 is positioned on the optical path, the light from the fundus of the patient's eye is reflected by the switching mirror 8, and passes through an imaging lens 9 and is reflected by a mirror 10 to form a fundus image on a light receiving plane 11 in a second photographing system.

As described above, the conventional ophthalmoscopic camera illumination apparatus using an annular slit forms a light source image on the annular slit. For this reason, only a part of the illumination light that forms the light source image passes through the annular aperture of the annular slit. Also, the light source image formed on the annular slit is brighter in the center than in the periphery. Therefore, in the conventional technology, a fundus is illuminated only with light from the peripheries of the image of the light source on the annular slit; this is an inefficient way of using the illumination light from the light source.

The present invention shown in this embodiment in FIG. 1 is capable of taking the light from the image of the light source into the entering end 22A of the cone-shaped reflective member 22 without a substantial loss in light intensity; it also guides the incoming light to the emitting end 22D and emits the light as an annular flux. This technique makes it possible to utilize the light from the light source without substantial loss in light intensity to illuminate a fundus with a reasonably bright illumination light. As a result, a bright eyeground image can be obtained without using a large power source even for high magnification photography; a bright eyeground image can be obtained with less power consumption for low magnification photography.

Also, the cone-shaped reflective member 22 of this embodiment can be compact taking advantage of its structure. Therefore, unlike the conventional technology using optical fibers with limited flexibility, the entire apparatus can be made miniaturized.

Figure 3:
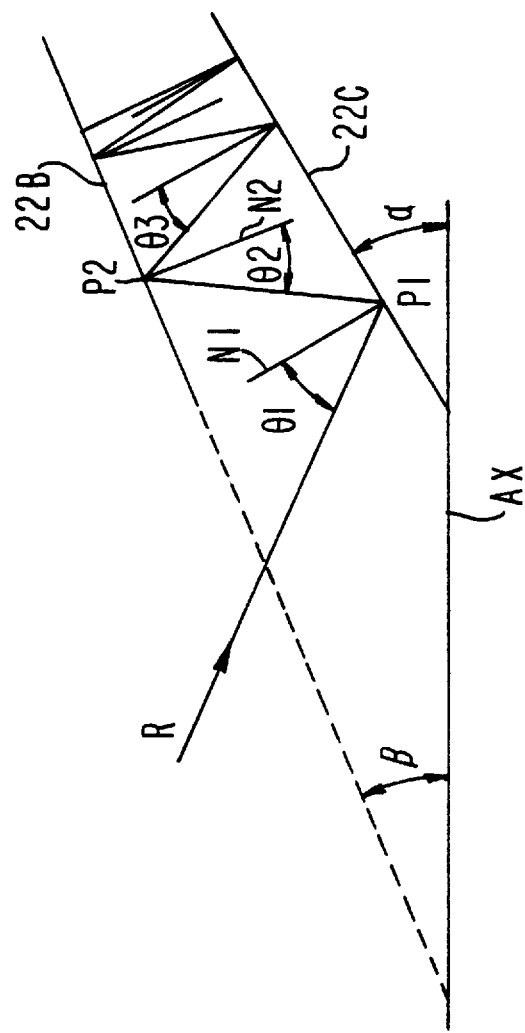

In FIG. 3, the cone-shaped reflective member 22 is a hollow member formed such that the space between the outer reflective surface 22B and the inner reflective surface 22C is unfilled. The apical angle made by the inner reflective surface 22C with the optical axis AX is α; the angle made by the outer reflective surface 22B with the optical axis AX is β.

Therefore, an incident light ray R entering at a certain angle with respect to the optical axis AX in FIG. 3 is reflected at a point P1 on the inner reflective surface 22C, and enters a point P2 on the outer reflective surface 22B. The angle made by the right ray R with a normal N1 of the inner reflective surface 22C at the point P1 at that time is θ1.

In the same manner, the following equation (1) {text reads (2)} represents the angle θ2 made by the light ray R with a normal N2 of the outer reflective surface 22B at the point P2:
[Equation 1]

$$\theta2 = \theta1 - (\alpha - \beta) \qquad (1)$$

As shown in FIG. 3, if the angle α is larger than the angle β, the angle of incidence θ2 at the outer reflective surface 22B is smaller than the angle of incidence θ1 at the inner reflective surface 22C. As a result, the light ray R reflected repeatedly in the hollow space inside of the cone-shaped reflective member 22, instead of emerging from the emitting end 22D, returns to the entering end 22A. For this reason, the apical angle β of the outer reflective surface 22B of the cone-shaped reflective member 22 needs to be larger than the apical angle α of the inner reflective surface 22C.

Note that the above mentioned embodiment uses a cone-shaped reflective member 22 in which the space between the outer reflective surface 22B and the inner reflective surface 22C is made hollow. However, the outer reflective surface and the inner reflective surface may be respectively formed as a single unit made of glass or resin to fill the space between the outer reflective surface and the inner reflective surface.

Figure 4:
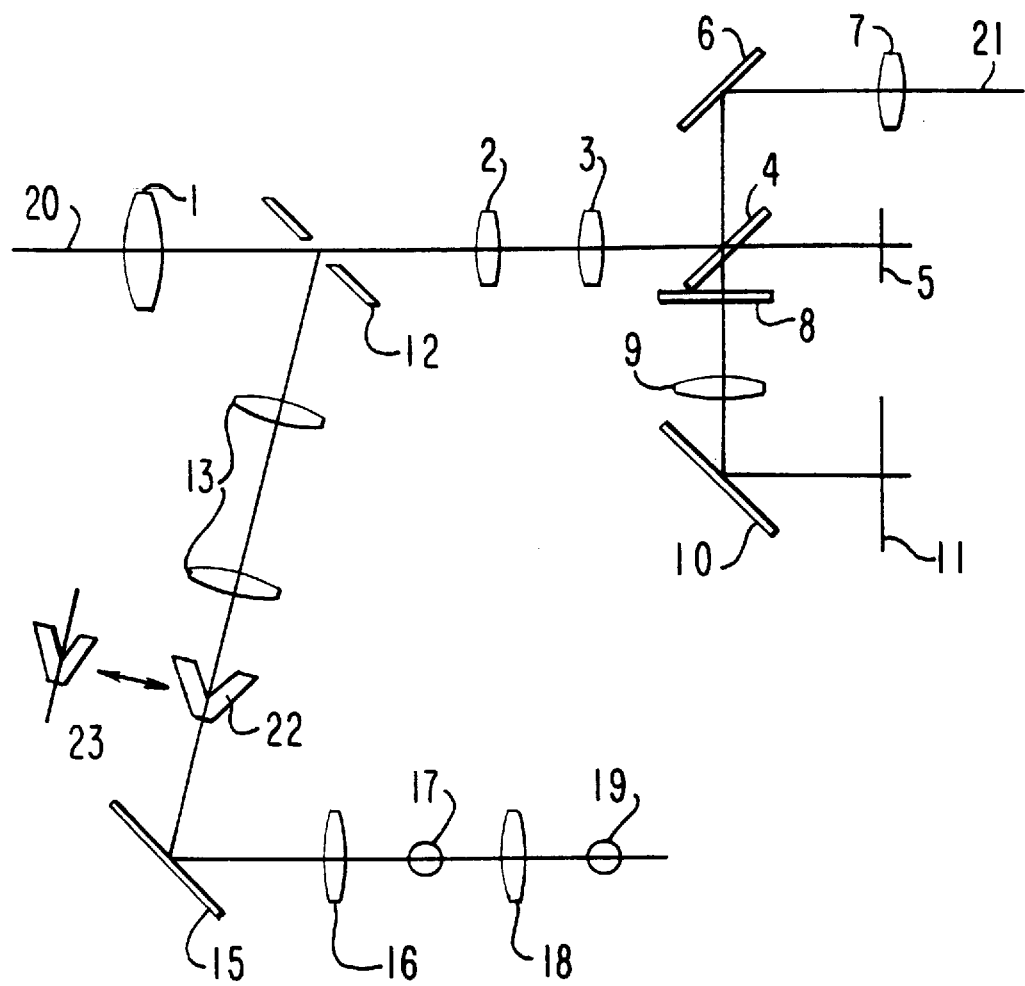

The modified example in FIG. 4 has the same configuration as the embodiment in FIG. 1, except that the cone-shaped reflective member 22 is switchable with another cone-shaped reflective member 23. Therefore, the components in FIG. 4 having the same function as those of the embodiment in FIG. 1 are numbered the same as in FIG. 1.

In the modified example in FIG. 4, a plurality of cone-shaped reflective members having a different diameter of annular emitting end are prepared so that they can be arbitrary selected according to the size of pupil of the patient's eye. Consequently, a optimal annular illumination can be provided according to the size of pupil of the patient's eye.

As described above, the ophthalmoscopic illumination apparatus of the present invention efficiently uses the light from the light source image without a substantial loss in light intensity so that the fundus is illuminated with a reasonably bright illumination light. As a result, a bright eyeground image can be obtained without using a large power supply even for high magnification photography and a bright eyeground image can be obtained with a less power consumption for low magnification photography.

Also, the annular flux forming means of the present invention can be constructed structurally on a small scale. Therefore, unlike the conventional apparatus using optical fibers which limit the bendable angle, the entire apparatus of the present invention can be made compact.

Various modifications, additions and substitutions will become possible for those skilled in the art after receiving the teachings of the present disclosure without departing from the scope and spirit thereof as disclosed in the accompanying claims.

I claim:

1. An ophthalmoscopic illumination apparatus which illuminates a fundus of a patient's eye for an ophthalmoscopic camera for photographing the fundus through an objective lens, comprising:

a light source for supplying illumination light;

a condenser optical system for gathering said illumination light from said light source to form a light source image; and an annular flux forming means comprising:

an entering end positioned in the vicinity of a light source image forming position;

an annular emitting end;

an outer reflective surface formed between an outer periphery of said emitting end and the outer periphery of said entering end;

an inner reflective surface formed inside said outer reflective surface so as to be connected to the inner periphery of said emitting end, so that the illumination light entering said entering end is reflected at said outer reflective surface and said inner reflective surface, and guided to said emitting end to go out as an annular light from said emitting end; and wherein said annular light emerging from said emitting end of said annular flux forming means passes through said objective lens to form an annular illumination area in the vicinity of a pupil of the eye of a patient.

2. An ophthalmoscopic illumination apparatus as set forth in claim 1, wherein the angle made by said outer reflective surface with the optical path is larger than that by said inner reflective surface with the optical path.

3. An ophthalmoscopic illumination apparatus as set forth in claim 1 or 2, wherein said annular flux forming means is constructed such that a hollow space between said outer reflective surface and said inner reflective surface.

4. An ophthalmoscopic illumination apparatus as set forth in claim 3, wherein said annular flux forming means comprises another annular flux forming means which is switchable with said annular flux forming means, said another annular flux forming means having a different diameter at said emitting end than said annular flux forming means.

5. An ophthalmoscopic illumination apparatus as set forth in claim 2, wherein said annular flux forming means is constructed such that a space between said outer reflective surface and said inner reflective surface is filled.

6. An ophthalmoscopic illumination apparatus as set forth in claim 2, wherein said annular flux forming means comprises another annular flux forming means which is switchable with said annular flux forming means, said another annular flux forming means having a different diameter at said emitting end than said annular flux forming means.

7. An ophthalmoscopic illumination apparatus, as set forth in claim 1, wherein said annular flux forming means is constructed such that a space between said outer reflective surface and said inner reflective surface.

8. An ophthalmoscopic illumination apparatus as set forth in claim 7, wherein said annular flux forming means comprises another annular flux forming means which is switchable with said annular flux forming means, said another annular flux forming means having a different diameter at said emitting end than said annular flux forming means.

9. An ophthalmoscopic illumination apparatus, as set forth in claim 1, wherein said annular flux forming means is constructed such that a space between said outer reflective surface and said inner reflective surface is filled.

10. An ophthalmoscopic illumination apparatus as set forth in claim 1, wherein said annular flux forming means comprises another annular flux forming means which is switchable with said annular flux forming means, said another annular flux forming means having a different diameter at said emitting end than said annular flux forming means.

11. An ophthalmoscopic illumination apparatus as set forth in claim 1, wherein the flux forming means forms an annular illumination in the vicinity of the pupil of the patient's eye through an objective lens.

* * * * *